United States Patent [19]

Giroux et al.

[11] 4,210,665

[45] Jul. 1, 1980

[54] USE OF α,α'-DITHIOBIS(β-ARYLACRYLIC ACID) DERIVATIVES IN HEAVY METAL POISONING

[75] Inventors: Eugene L. Giroux, Cincinnati, Ohio; Nellikunja J. Prakash; Paul J. Schechter, both of Strasbourg, France

[73] Assignee: Merrell Toraude et Campagnie, Strasbourg, France

[21] Appl. No.: 16,940

[22] Filed: Mar. 2, 1979

[51] Int. Cl.² .................... A61K 31/19; A61K 31/34; A61K 31/38; A61K 31/40
[52] U.S. Cl. .................................. 424/275; 424/274; 424/285; 424/317
[58] Field of Search .................. 424/10, 274, 275, 285, 424/317

[56] References Cited
U.S. PATENT DOCUMENTS 4,124,718  11/1978  Giroux et al. .................... 424/274

OTHER PUBLICATIONS

Compaigne, et al., J. Org. Chem. 21, 32, (1956).
Haskell, et al., J. Med. Chem. 13, 697, (1970).
Schneller, et al., C.A., vol. 81, (1974), 37492k.

Primary Examiner—Allen J. Robinson
Attorney, Agent, or Firm—Stephen L. Nesbitt; L. Ruth Hattan; Eugene O. Retter

[57] ABSTRACT

This invention relates to a novel method for combatting heavy metal poisoning which comprises administering a compound of the formula:

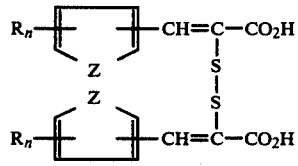

wherein Z is C=C, O, S, NH; R is hydrogen, methyl, ethyl, hydroxy, methoxy, ethoxy, chlorine, bromine, fluorine, iodine or trifluoromethyl; and n is 1, 2 or 3.

5 Claims, No Drawings

USE OF α,α'-DITHIOBIS(β-ARYLACRYLIC ACID) DERIVATIVES IN HEAVY METAL POISONING

BACKGROUND OF INVENTION

While α,α'-dithiobis(β-arylacrylic acids) are known their utilization in therapeutics is quite rare. The compounds employed in the present invention are most commonly prepared by the procedures of E. Campaigne and R. Cline, J. Org. Chem. 21, 32 (1956) by oxidation of the corresponding α-mercapto-β-arylacrylic acids. Haskel et al., J. Med. Chem. 13, 697 (1970) has prepared and tested α,α'-dithiobis[β-(2-thienyl)acrylic acid] and α,α'-dithiobis[β-(2-chlorophenyl)acrylic acid] for neuraminidase inhibition activity. The use of the α-mercapto-β-arylacrylic acids in combatting heavy metal poisoning, in treating hypertension, and in zinc serum and tissue concentration enhancement is disclosed in copending U.S. application Ser. No. 892,187 filed March 31, 1978; allowed Jan. 15, 1979, to be issued Sept. 25, 1979, in U.S. Pat. No. 4,130,653 issued Dec. 19, 1978, and in U.S. Pat. No. 4,124,718 issued Nov. 7, 1978, respectively. No references more pertinent than these are known to the applicants.

SUMMARY OF THE INVENTION

This invention relates to a method of combatting poisoning resulting from heavy metals selected from zinc, cadmium, mercury, and copper in a patient in need thereof, by administering an α,α'-dithiobis(β-arylacrylic acid) of Formula I or a pharmaceutically acceptable nontoxic salt thereof

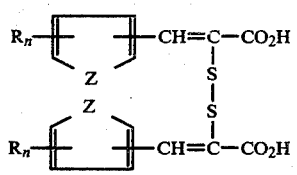

Formula I wherein Z is —C=C—, O, S, or NH; R is H, $CH_3$, $C_2H_5$, OH, $CH_3O$, $C_2H_5O$, Cl, Br, F, I, or $CF_3$; and n is 1, 2 or 3.

DETAILED DESCRIPTION OF THE INVENTION

It is apparent from the foregoing general Formula I that the compounds employed in the present invention are α,α'-dithiobis(β-thienylacrylic acids), α,α'-dithiobis(β-furylacrylic acids), α,α'-dithiobis(β-pyrrylacrylic acids), α,α'-dithiobis(β-phenylacrylic acids), and their pharmaceutically acceptable non-toxic salts thereof wherein the aromatic ring, that is, the thienyl, furyl, pyrryl, or phenyl rings may be further substituted with from 1 to 3 groups selected from methyl, ethyl, hydroxy, methoxy, ethoxy, chlorine, bromine, fluorine, iodine, or trifluoromethyl as illustrated, respectively, by the following Formulas II to V.

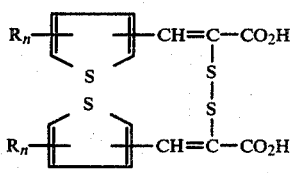

Formula II

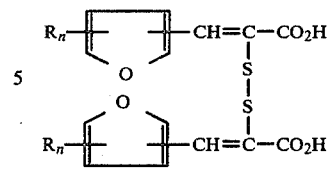

Formula III

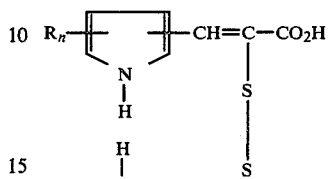

Formula IV

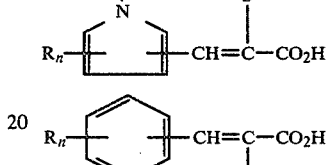

Formula V

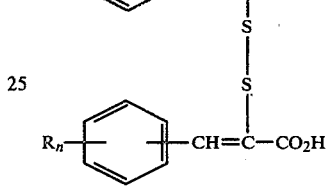

In the above general Formulas II to V, R and n have the meanings defined in Formula I.

In general Formulas II and III, it is preferred that the acrylic acid moiety, that is,

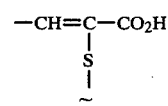

be attached to the 2-position of the furan or thiophene ring, and it is more preferred that within these groups of compounds when R is other than hydrogen that n be equal to 1 with the substituent as represented by R being attached at the 5-position of the furan or thiophene ring in the practice of the present invention. In general Formulas I to V, preferred substituent groups as represented by R are hydrogen, methyl, ethyl, hydroxy, methoxy, ethoxy, chlorine, bromine and trifluoromethyl.

Illustrative species within the general Formula I are compounds wherein the aryl group is phenyl or substituted phenyl, for example, 2-, 3- or 4-methyl, 2-3- or 4-ethyl, 2-, 3- or 4-bromo, 2-, 3- or 4-chloro, 2-, 3- or 4-fluoro, 2-iodo, 2,4-dichloro, 2,3-dichloro, 2,3,4-trichloro, 2-trifluoromethyl, 3-trifluoromethyl, 2-trifluoromethyl-3-chloro, 2-, 3- or 4-hydroxy, 2-, 3- or 4-methoxy, 2-, 3- or 4-ethoxy, 2-hydroxy-3-methoxy, 3-hydroxy-4-methoxy, 3-methoxy-4-hydroxy, 3-ethoxy-4-hydroxy, 2,3-dimethoxy, 2,4-dimethoxy, 2,5-dimethoxy, 2,6-dimethoxy, 3,4-dihydroxy, 3,4,5-trimethoxy, 2,3,4-trimethoxy, 3,5-dibromo-4-hydroxy; or other aryl groups in place of phenyl, namely, 2-furyl, 5-trifluoro-2-furyl, 5-methyl-2-furyl, 5-ethoxy- or 5-methoxy-2-furyl, 5-chloro-2-furyl; 3-furyl; 2-thienyl, or substituted thienyl, for example, 3-methyl, 5-methyl, 5-ethyl, 5-chloro, 5-bromo, 3-methoxy, 5-methoxy; 3-thienyl; 2-pyrryl; and 3-pyrryl; and pharmaceutically acceptable non-toxic salts thereof illustratively, sodium, potassium, calcium, aluminum, zinc, ammonium salts, amine salts, for example, trialkylamine, such as triethylamine, dibenzylamine, glucosamine, of each of the above acids.

The present invention provides a novel method of treating or combatting the ill effects of the heavy metal ions of zinc, mercury, cadmium, or copper resulting from excessive internal accumulation of said metals in a patient. Internal accumulation of the heavy metals in excessive amounts may result, for example, from ingestion or inhalation of said metal. The term excessive amounts is intended to mean any amount which may result in ill effects or poisoning. Commonly known ill effects which may result from poisoning with the enumerated heavy metals include gastric cramps, vomitting, diarrhea, headache, shock, cough, coma, renal failure, nephrosis, ataxia, mania, convulsions, insomnia, gastrointeritis, anuria, uremia, burning mouth pain, and colitis. The present invention provides a novel method of detoxifying a patient from the intoxicating or poisoning effects of excess amounts of the heavy metals.

The most preferred embodiment of this invention is the use of compounds of general Formula I or a pharmaceutically acceptable salt thereof wherein R is hydrogen in combatting poisoning resulting from excess amounts of the heavy metals selected from the group consisting of zinc, cadmium, copper and mercury.

As used herein the term patient is taken to mean warm blooded animals, for example, birds such as chickens and turkeys and mammals such as primates, humans, sheep, horses, bovine cows and bulls, pigs, dogs, cats, rats, and mice. More particularly, the term patient with regard to heavy metal poisoning is a warm blooded animal capable of forming the metal binding protein known as metallothionein and suffering the ill effects of the heavy metal ions of zinc, mercury, cadmium or copper.

In practising the present invention the compounds of Formula I or a salt thereof either alone or in combination with acceptable pharmaceutical carriers are administered to the patient to be treated either orally or parenterally, for example, subcutaneously or intravenously. Compounds of general Formula I may be used in combination with one another. A preferred mode of administration of the compounds of general Formula I in the practice of the present invention is oral administration.

The compounds of Formula I may be formulated for oral administration as solid or liquid unit dosage forms. The solid dosage forms can be tablets, coated or uncoated; capsules, hard or soft; powders, granules; pills, enteric coated if desired. Solid diluents and carriers may be lactose, starch or other innocuous material with the usual tableting adjuncts as desired. Liquid oral compositions may be dispersions, suspensions, elixirs, syrups or simple solutions in aqueous vehicle. Polyethylene glycols including polyethylene glycol 300 have been found convenient oral vehicles. The term unit dosage form as used in the specification and claims means physically discrete units suitable for unitary administration, each unit containing a predetermined quantity of active ingredient to achieve the desired therapeutic effect in association with the pharmaceutical carrier. Sterile, intraperitoneal formulation with physiologically acceptable vehicle, for example, saline, optionally buffered can also be utilized.

The amount of compound administered will vary over a wide range depending upon the patient to be treated and the severity of the ill effects or poisoning and will be any amount effective in treating or combatting said ill effects of poisoning of from about 0.1 mg/kg to 20.0 mg/kg of body weight of the patient per day. For example, a unit dosage form may suitably contain about 250 mg of active ingredient as represented by Formula I or salt thereof.

The utility of the compounds of general Formula I in combatting poisoning resulting from zinc, cadmium, mercury and copper can be demonstrated in animals poisoned with the above mentioned metals, by administering a compound of Formula I and subsequently noting a lessening of the symptoms of poisoning and a decrease in the mortality rate of the test animals.

The $\alpha,\alpha'$-dithiobis($\beta$-arylacrylic acids) are more stable than the corresponding $\alpha$-mercapto-$\beta$-arylacrylic acids in solution and solid form and, accordingly, are superior from a pharmacological viewpoint.

Preparation of the $\alpha,\alpha'$-dithiobis($\beta$-arylacrylic acids) of applicability herein is according to the methods described by E. Campaigne and P. E. Cline, J. Org. Chem. 21, 32 (1956) by oxidation of the corresponding $\alpha$-mercapto-$\beta$-arylacrylic acid with either iodine in ethanol or benzoyl peroxide in benzene according to the general scheme:

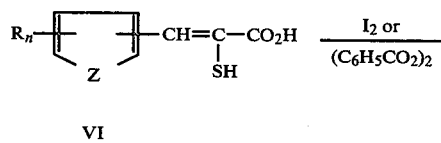

VI

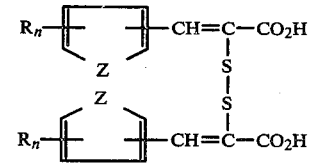

I wherein Z, R and n are as defined hereinabove. Additionally, other oxidizing agents may be used in place of the iodine or benzoyl peroxide mentioned above such as hydrogen peroxide or molecular oxygen. The desired salts can be prepared by reaction between the hydroxide, carbonate or other basic metal, ammonium, or amine compound and the free $\alpha,\alpha'$-dithiobis($\beta$-arylacrylic acid) in the usual manner.

The following specific examples further illustrate the preparation of compounds employed in the instant invention.

EXAMPLE 1

$\alpha,\alpha'$-Dithiobis[$\beta$-(2-furyl)acrylic acid]

Iodine is added to a solution of 100 g of potassium iodide in 500 ml of water to saturation. This saturated solution is added dropwise to a solution of $\alpha$-mercapto-$\beta$-(2-furyl)acrylic acid in 500 ml of acetonitrile and 30 ml of water until the color of iodine persists. The crude product which precipitates is recrystallized from methanol. M.P. 215° C.

EXAMPLE 2 $\alpha,\alpha'$-Dithiobis[$\beta$(2-thienyl)acrylic acid]

Substituting $\alpha$-mercapto-$\beta$-(2-thienyl)acrylic acid for $\alpha$-mercapto-$\beta$-(2-furyl)acrylic acid in the procedure of Example 1 gives $\alpha,\alpha'$-dithiobis[$\beta$(2-thienyl)acrylic acid].

EXAMPLE 3

α,α'-Dithiobis(β-phenylacrylic acid)

Substituting α-mercapto-β-phenylacrylic acid for α-mercapto-β-(2-furyl)acrylic acid in the procedure of Example 1 gives α,α'-dithiobis(β-phenylacrylic acid).

We claim:

1. A method of combatting poisoning resulting from heavy metals selected from the group consisting of zinc, cadmium, copper and mercury in a patient in need thereof which comprises administering to said patient an effective amount of a compound of the following formula:

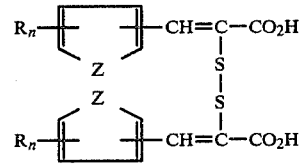

wherein Z is C=C, O, S, or NH; R is H, $CH_3$, $C_2H_5$, OH, $CH_3O$, $C_2H_5O$, Cl, Br, F, I, or $CF_3$; and n is 1, 2 or 3; or a pharmaceutically acceptable non-toxic salt thereof.

2. The method of claim 1 wherein R is H, $CH_3$, $C_2H_5$, OH, Cl, Br, or $CF_3$.

3. The method of claim 2 wherein Z is O or S and the aromatic ring is substituted at the 2,5-positions.

4. The method of claim 1 wherein the active ingredient is α,α'-dithiobis[β-(2-furyl)acrylic acid] or a pharmaceutically acceptable non-toxic salt thereof.

5. The method of claim 1 wherein the active ingredient is α,α'-dithiobis[β-(2-thienyl)acrylic acid] or a pharmaceutically acceptable non-toxic salt thereof.

* * * * *